United States Patent
Chen

(10) Patent No.: US 9,968,327 B2
(45) Date of Patent: May 15, 2018

(54) X-RAY IMAGE DETECTION SYSTEM AND METHOD OF CONTROLLING THE SAME

(71) Applicant: InnoLux Corporation, Miao-Li County (TW)

(72) Inventor: Yu-Heing Chen, Miao-Li County (TW)

(73) Assignee: INNOLUX CORPORATION, Miao-Li County (TW)

( * ) Notice: Subject to any disclaimer, the term of this patent is extended or adjusted under 35 U.S.C. 154(b) by 0 days. days.

(21) Appl. No.: 15/462,938

(22) Filed: Mar. 20, 2017

(65) Prior Publication Data

US 2017/0273655 A1    Sep. 28, 2017

(30) Foreign Application Priority Data

Mar. 25, 2016    (CN) .......................... 2016 1 0176660

(51) Int. Cl.
*A61B 6/00*    (2006.01)

(52) U.S. Cl.
CPC .............. *A61B 6/54* (2013.01); *A61B 6/4208* (2013.01)

(58) Field of Classification Search
CPC .................................. G01V 5/12; G21K 1/02
See application file for complete search history.

(56) References Cited

U.S. PATENT DOCUMENTS

| | | | | |
|---|---|---|---|---|
| 6,094,473 A * | 7/2000 | Yu | ............................ | H05G 1/38 378/108 |
| 6,271,785 B1 * | 8/2001 | Martin | ................... | H04N 3/155 341/155 |
| 7,368,724 B2 * | 5/2008 | Morii | ................ | H01L 27/14658 250/370.01 |
| 7,456,409 B2 * | 11/2008 | Dhurjaty | ................... | G01T 1/17 250/369 |
| 7,638,773 B2 * | 12/2009 | Kuwabara | .............. | G03B 42/04 250/370.08 |
| 8,705,700 B2 * | 4/2014 | Eguchi | ................. | A61B 6/4233 378/116 |
| 9,366,766 B2 * | 6/2016 | Okada | ....................... | H04N 5/32 |
| 9,379,730 B2 * | 6/2016 | Moro | .................... | G01J 1/0238 |
| 9,513,379 B2 * | 12/2016 | Nishino | ................. | A61B 6/548 |
| 9,782,144 B2 * | 10/2017 | Kuwabara | ................ | A61B 6/54 |
| 2001/0012070 A1 * | 8/2001 | Enod | ........................ | H04N 5/32 348/302 |

(Continued)

*Primary Examiner* — David Porta
*Assistant Examiner* — Djura Malevic
(74) *Attorney, Agent, or Firm* — Bacon & Thomas, PLLC

(57) ABSTRACT

An X-ray image detection system includes a charge accumulation device, a switch device, a comparator device and an analog to digital converter. The charge accumulation device receives current produced by a pixel and converts the current to a voltage signal. The switch device has an input terminal, a first output terminal, and a second output terminal. The input terminal is connected to the charge accumulation device to receive the voltage signal. The comparator device is connected to the first output terminal for generating first or second indication signal according to the voltage signal. The analog to digital converter is connected to the second terminal. When the first indication signal is generated, the input terminal of the switch device is connected to the first output terminal. When the second indication signal is generated, the input terminal of the switch device is connected to the second output terminal.

12 Claims, 10 Drawing Sheets

(56) References Cited

U.S. PATENT DOCUMENTS

| | | | | |
|---|---|---|---|---|
| 2002/0186813 | A1* | 12/2002 | Tamura | H04N 5/321 378/98.8 |
| 2003/0038242 | A1* | 2/2003 | Endo | H01L 27/14603 250/370.14 |
| 2005/0061955 | A1* | 3/2005 | Endo | G01T 1/2928 250/214 R |
| 2009/0087073 | A1* | 4/2009 | Kito | A61B 6/00 382/132 |
| 2010/0277592 | A1* | 11/2010 | Yokoyama | G01T 1/1647 348/162 |
| 2013/0039462 | A1* | 2/2013 | Morton | G01V 5/0041 378/57 |
| 2015/0001379 | A1* | 1/2015 | Moro | G01J 1/0238 250/214 DC |

* cited by examiner

X-RAY IMAGE DETECTION SYSTEM AND METHOD OF CONTROLLING THE SAME

BACKGROUND

1. Field of the Invention

The present disclosure relates to the technical field of detections and, more particularly, to an X-ray image detection system and a method of controlling the same.

2. Description of Related Art

FIG. 1 is a schematic diagram of a prior X-ray imaging system 100. The X-ray imaging system 100 consists of an X-ray generating apparatus 110 and an X-ray imaging apparatus 120. The X-ray generating apparatus 110 includes an X-ray source 111, a source control unit 112 for controlling the operation of the X-ray source 111 and an irradiation switch 113. The X-ray imaging apparatus 120 consists of a ray image detection apparatus 121, a support frame 122. The ray image detection apparatus 121 consists of a fluorescent screen and an X-ray film. In the X-ray photographing for medical image, by performing an exposure to the X-ray film, the X-ray image can be directly recorded and developed on the X-ray film, and thus the physical condition of a patient can be recorded.

Since recording the physical condition of patient by an X-ray film as aforementioned cannot satisfy the requirement of digitalization, there is another prior X-ray imaging system 200 provided as shown in FIG. 2, which introduces a new X-ray imaging apparatus 210. In the X-ray imaging apparatus 210, an X-ray flat panel detector (X-ray FPD) 211 replaces the ray image detection apparatus 121 that uses an X-ray film, and the imaging process of the X-ray flat panel detector 211 is controlled by a controller device 212. Then, the controller device 212 transmits the digital image of the patient to a display device 220.

Although the X-ray imaging system 200 in FIG. 2 can satisfy the requirement of image digitalization, the new X-ray imaging apparatus 210 is an additional component, which cannot synchronize with the early type X-ray generating apparatus 110. In order to solve the problem of synchronizing the new type X-ray imaging apparatus 210 with the early type X-ray generating apparatus 110, an automatic exposure detection (AED) is introduced.

FIG. 3 is the diagram of a prior X-ray flat panel detector 211, which includes an X-ray image detector 310, at least one integrator 320, and an analog to digital convertor (ADC) 330. The X-ray image detector 310 has at least one pixel 311. The amount of current produced by the at least one pixel corresponds to the amount of incident X-ray. In order to detect the X-ray produced by the X-ray generating apparatus 110, the X-ray image detector 3110, the at least one integrator 320 and the analog to digital convertor 330 are all in operation.

FIG. 4 is the timing diagram of the AED of the X-ray flat panel detector in FIG. 3. Please also refer to FIG. 2, FIG. 3 and FIG. 4. At the time $T_A$, after X-ray generating apparatus 110 generates an X-ray, the analog to digital convertor 330 will detect that the voltage of the point A has a significant change (for example, over a threshold), and will generate a signal to notify the controller device 212 of such, and the controller device 212 will clean up the charges of the at least one pixel 311 in a very short time $T_B$ (for example, 1 ms). Then, after the time $T_C$, the remaining X-ray data is collected and an image is formed. In order to achieve the function of AED, in the present time, the analog to digital convertor 330 must always stay in operating mode and thus consume high power, which cannot satisfy the trend of power saving. Thus, there is a need for the prior X-ray flat panel detector to be improved.

SUMMARY

The main purpose of the present disclosure is to provide an X-ray image detection system and a method of controlling the same, in which a comparator device is used to monitor and determine whether an X-ray radiation has started or not. Only when determining that the X-ray radiation has started, an analog to digital convertor will be woken up from a sleep mode to an operating mode, so as to save the power of the analog to digital convertor. The technology of the present disclosure is particularly suitable for a portable X-ray FPD product.

According to a feature of the present disclosure, the present disclosure provides an X-ray image detection system, which comprises a charge accumulation device, a switch device, a comparator device and a first analog to digital convertor. The charge accumulation device receives a current produced by at least one pixel, and converts the current to a voltage signal. The switch device has an input terminal, a first output terminal and a second output terminal. The input terminal is connected to the charge accumulation device to receive the voltage signal. The comparator device is connected to the first output terminal, generating a first indication signal or a second indication signal according to the voltage signal. The first analog to digital convertor is connected to the second output terminal. Wherein when the first indication signal is generated, the input terminal of the switch device is connected to the first output terminal thereof, when the second indication signal is generated, the input terminal of switch device is connected to the second output terminal thereof.

According to another feature the present disclosure, the present disclosure provides a method for detecting an X-ray image, which is applicable to an X-ray image detection system, the X-ray image detection system includes an X-ray image detector, a charge accumulation device, a comparator device and an analog to digital convertor. The X-ray image detector has at least one pixel. The at least one pixel produces an amount of current corresponding to an amount of incident X-ray. In the method: the charge accumulation device is used to receive the amount of the current produced by the at least one pixel, and convert the amount of the current to a voltage signal; the comparator device is used to determine if the X-ray radiation starts according to the voltage signal; when the X-ray radiation has not started, the comparator device generates a first indication signal; when the X-ray radiation has started, the comparator device generates a second indication signal. When the first indication signal is generated, a first current is enabled to flow through the analog to digital convertor; when the second indication signal is generated, a second current is enabled to flow through the analog to digital convertor, and the analog to digital convertor converts the voltage signal to a digital signal, wherein the first current is greater than or equal to zero, and smaller than a half of the second current.

DETAILED DESCRIPTION OF THE PREFERRED EMBODIMENT

Figure 1:
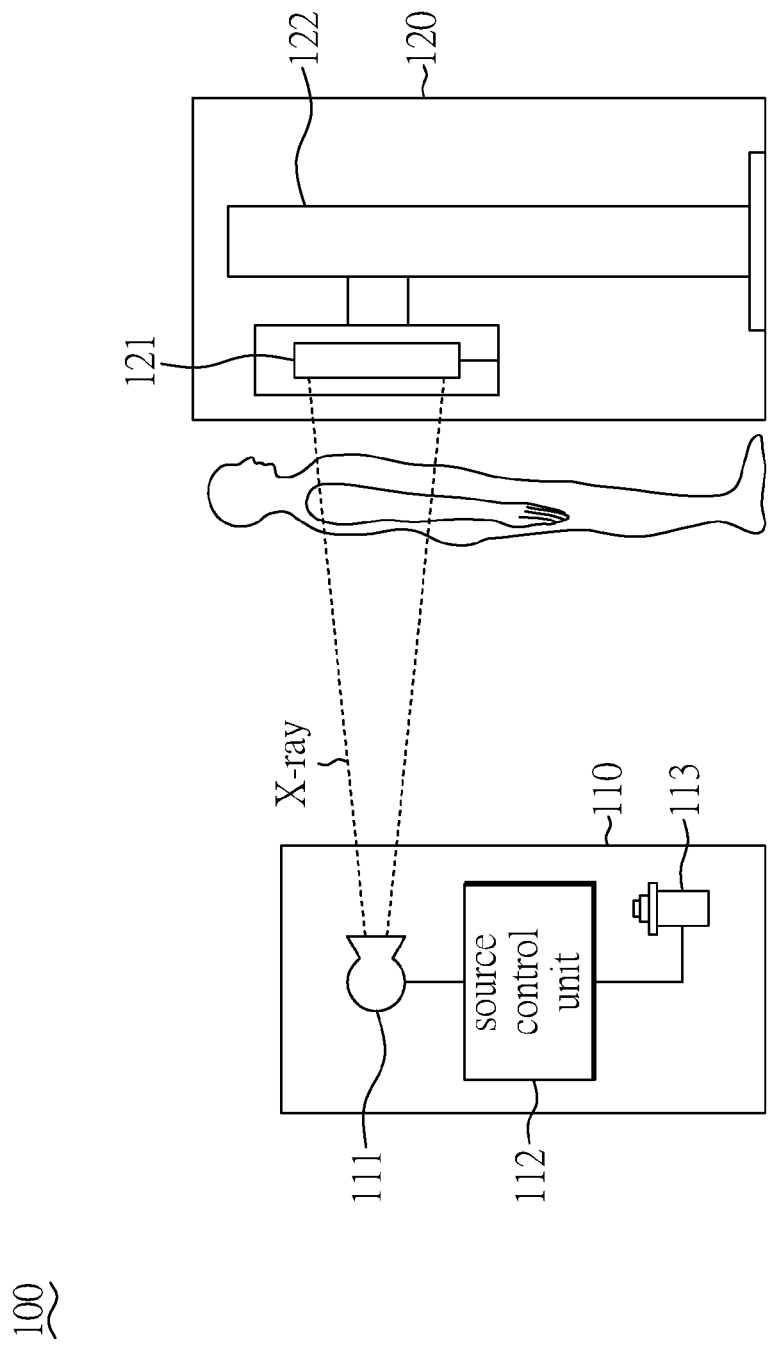
FIG. 1 is the schematic diagram of a prior X-ray imaging system.
Figure 2:
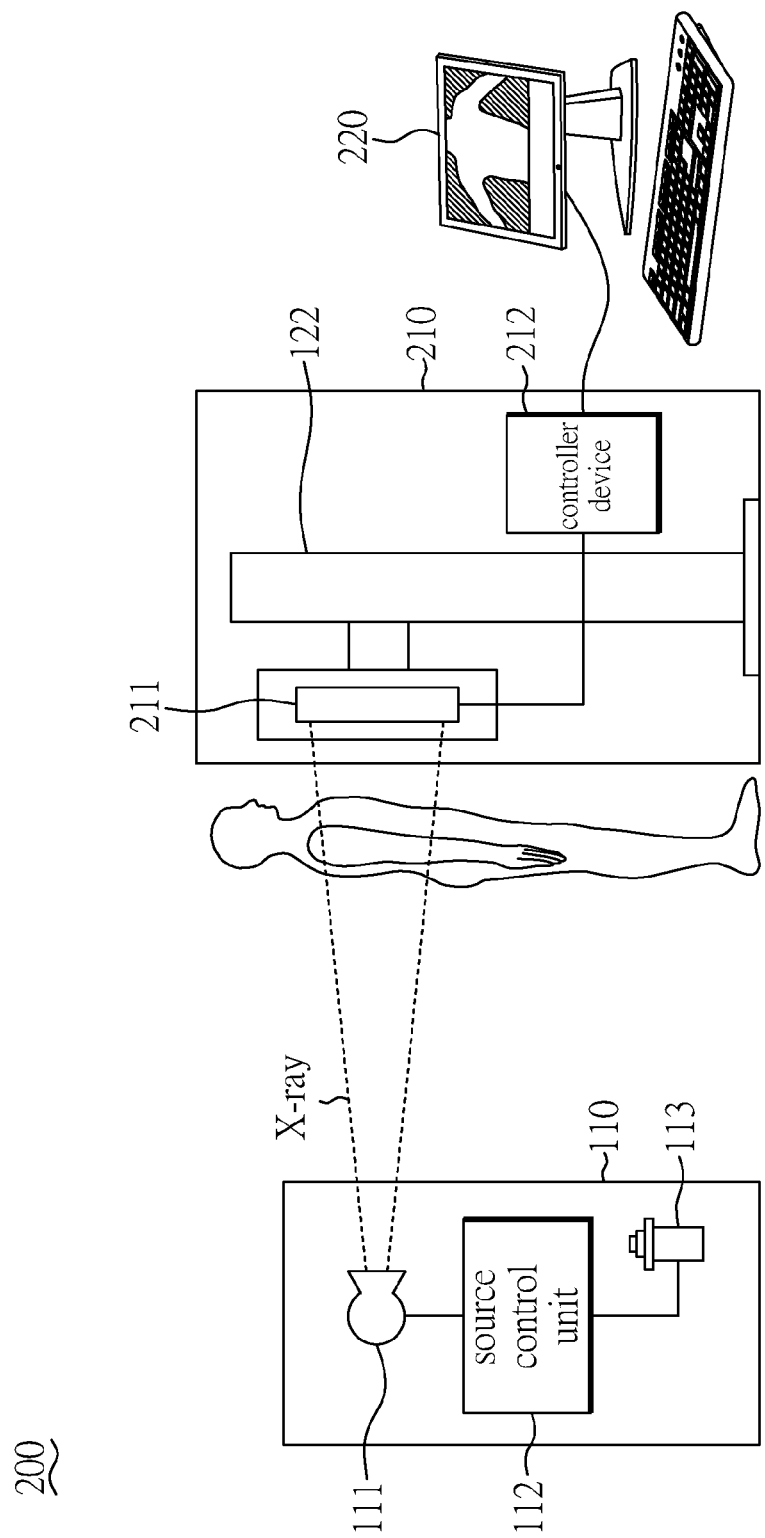
FIG. 2 is the schematic diagram of another prior X-ray imaging system.
Figure 3:
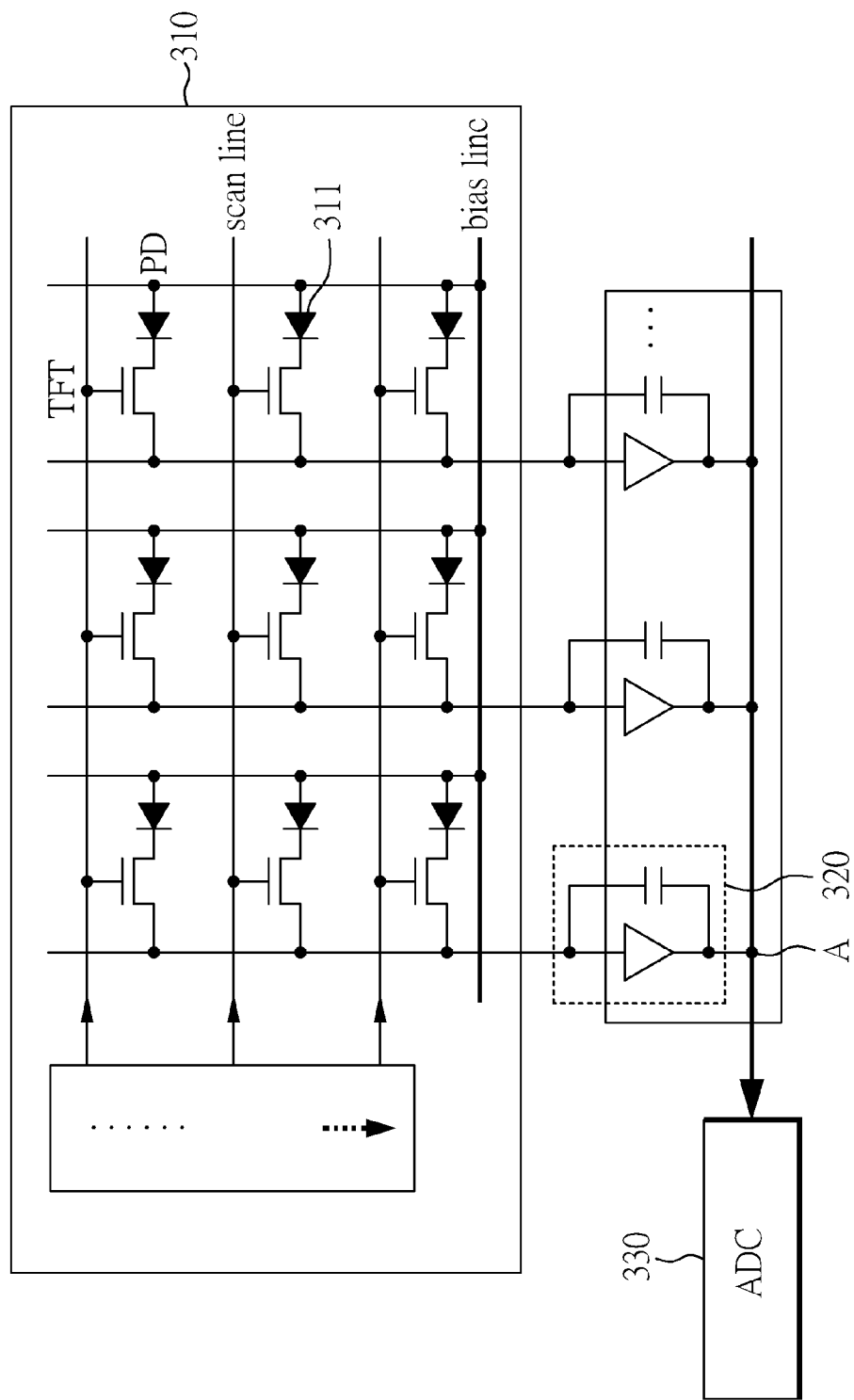
FIG. 3 is the schematic diagram of a prior X-ray flat panel detector.
Figure 4:
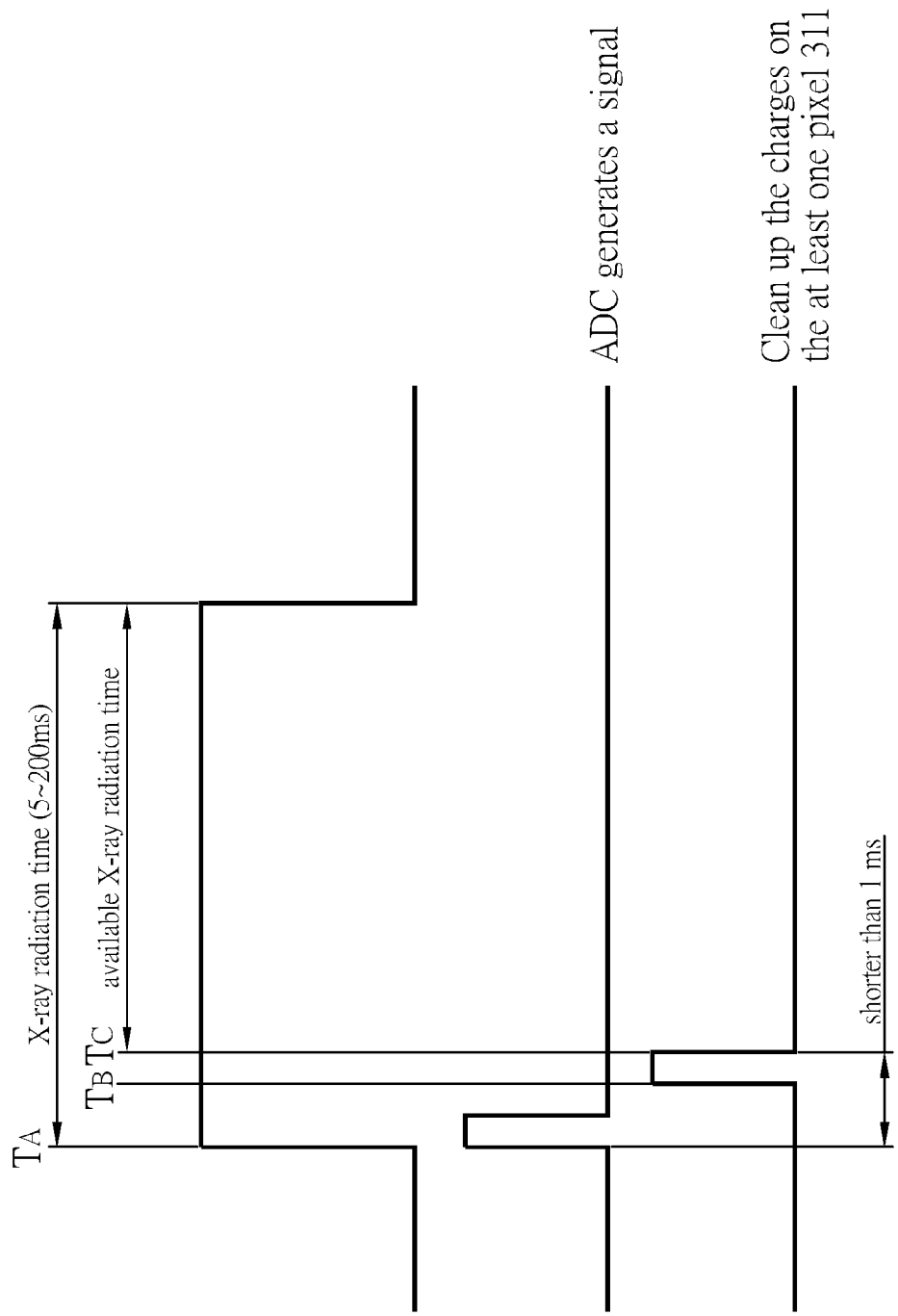
FIG. 4 is the timing diagram for the AED of the X-ray flat panel detector in FIG. 3.
Figure 5:
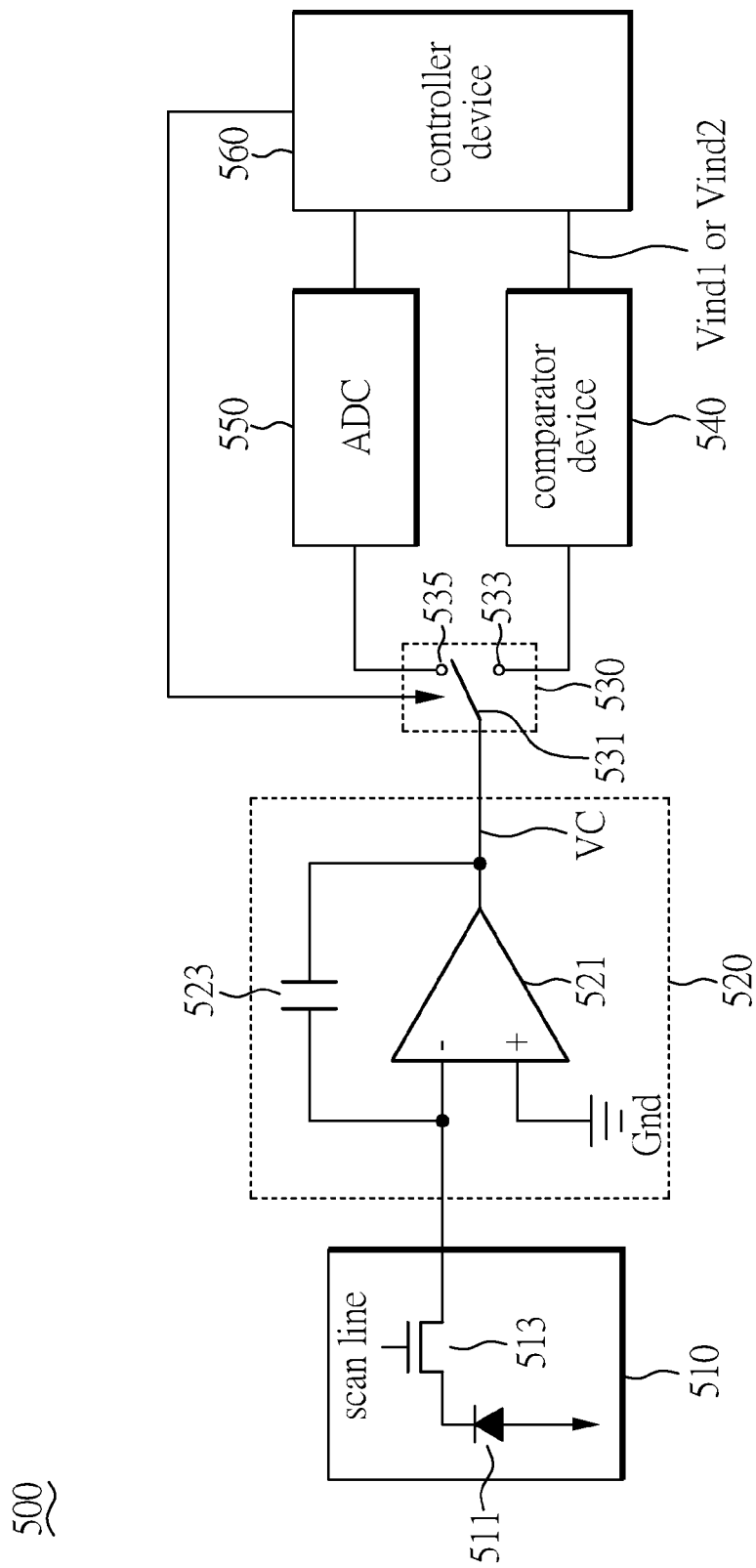
FIG. 5 is the schematic diagram of an X-ray image detection system according to the present disclosure.

FIG. 5 is a schematic diagram of the X-ray image detection system 500 according to the present disclosure. As shown in FIG. 5, the X-ray image detection system 500 includes an X-ray image detector 510, a charge accumulation device 520, a switch device 530, a comparator device 540, an analog to digital convertor (ADC) 550 and a controller device 560.

The X-ray image detector 510 has at least one pixel 511. The pixel 511 includes a switch element 513. The amount of current produced by the at least one pixel 511 corresponds to the amount of incident X-ray. The switch element 513 is connected to the charge accumulation device 520 for transmitting the current produced by the at least one pixel 511 to the charge accumulation device 520.

The charge accumulation device 520 receives the current produced by at least one pixel 511, and converts the current to a voltage signal VC. The charge accumulation device 520 includes an operational amplifier 521 and a capacitor 523. An inverted input terminal (−) of the operational amplifier 521 is connected to the switch element 513 and an end of the capacitor 523. The other end of the capacitor 523 is connected to the output terminal of the operational amplifier 521. A non-inverted input terminal (+) of the operational amplifier 521 is connected to a low voltage (gnd).

The switch device 530 has an input terminal 531, a first output terminal 533 and a second output terminal 535. The input terminal 531 is connected to the charge accumulation device 520 for receiving the voltage signal VC.

The comparator device 540 is connected to the first output terminal 533 for generating a first indication signal Vind1 or a second indication signal Vind2 according to the voltage signal. That is, the comparator device 540 determines if the X-ray radiation starts according to the voltage signal VC. In default, the input terminal 531 of the switch device 530 is connected to the first output terminal 533 thereof. When the X-ray radiation has not started, the comparator device 540 generates a first indication signal Vind1 (for example, a low voltage); when the X-ray radiation has started, the comparator device 540 generates a second indication signal Vind2 (for example, a high voltage).

The output terminal of the controller device 560 is connected to the switch device 530. The input terminal of the controller device 560 is connected to the comparator device 540 and the analog to digital convertor 550, wherein when the first indication signal Vind1 is generated, the input terminal 531 of the switch device 530 is connected to the first output terminal 533 thereof, and when the second indication signal Vind2 is generated, the input terminal 531 of the switch device 530 is connected to the second output terminal 535 thereof. When the controller device 560 receives the first indication signal Vind1, the input terminal 531 of the switch device 530 is connected to the first output terminal 533 thereof. When the controller device 560 receives the second indication signal Vind2, it connects the input terminal 531 of the switch device 530 to the second output terminal 535 thereof. Since the analog to digital convertor 550 is connected to the second output terminal 535, the voltage signal VC can be converted to a digital signal.

When the input terminal 531 of the switch device 530 is connected to the first output terminal 533 thereof, a first current flows through the analog to digital convertor 550. When the input terminal 531 of the switch device 530 is connected to the second output terminal 535 thereof, a second current flows through the analog to digital convertor 550. In this case, the first current is greater than or equal to zero and is smaller than a half of the second current.

The present disclosure introduces a low power consumption comparator device 540. When waiting the X-ray generating apparatus 110 to produce an X-ray, the analog to digital convertor 550 is in a sleep mode. When the X-ray generating apparatus 110 is producing the X-ray, due to being radiated by the X-ray, the at least one pixel 511 will produce an amount of current corresponding to an amount of incident X-ray. The current produced by the at least one pixel 511 will charge the capacitor 523. Thus, the output terminal of the operational amplifier 521 generates a voltage signal VC. The comparator device 540 can determine if the X-ray radiation starts according to the voltage signal VC. When the comparator device 540 determines that the X-ray radiation has started, it generates a second indication signal Vind2. When the controller device 560 receives the second indication signal Vind2, which indicates that the X-ray generating apparatus 110 is producing X-ray, the controller device 560 will control the input terminal 531 of the switch device 530 to connect to the second output terminal 535 thereof, as well as wakes up the analog to digital convertor 550 from the sleep mode to enter the operating mode. At this time, the second current, consumed by the analog to digital convertor 550, is much larger than the first current, consumed by the analog to digital convertor 550. Compared to the prior art in which the analog to digital convertor 550 has to detect the possible incident X-ray all the time with continuous consumption of the second current, the design in the present disclosure can achieve the purpose of power saving.

In one embodiment, the comparator device 540 can be a low-order analog to digital convertor, and the resolution of the low-order analog to digital convertor is lower than the resolution of the analog to digital convertor 550. The analog to digital convertor 550 mainly converts the current produced by the at least one pixel 511 to a digital signal, so as to generate X-ray image data of a patient. Thus, the analog to digital convertor 550 preferably has a resolution of 16 bits or more. Since the low-order analog to digital convertor is introduced to generate the first indication signal Vind1 or the second indication signal Vind2, it can be an analog to digital convertor with low resolution, such as of 6 bits or 8 bits, and this can achieve the purpose of power saving as well.

Figure 6B:
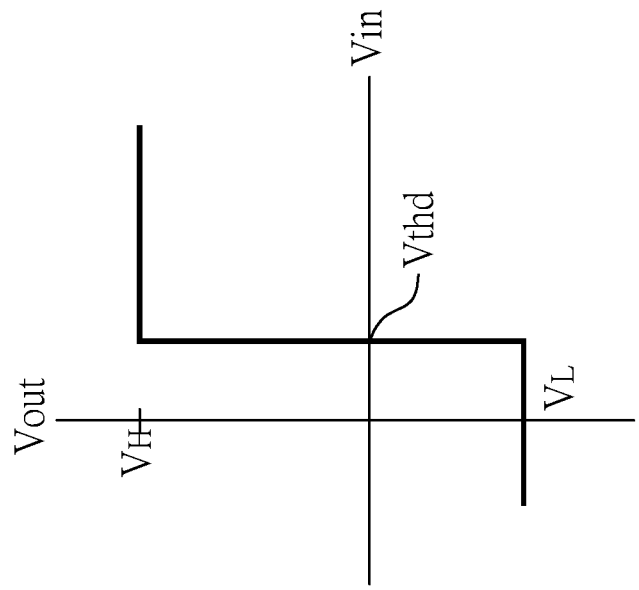
FIG. 6B is the graph showing the input/output characteristic of the operational amplifier according to the present disclosure.
Figure 6A:
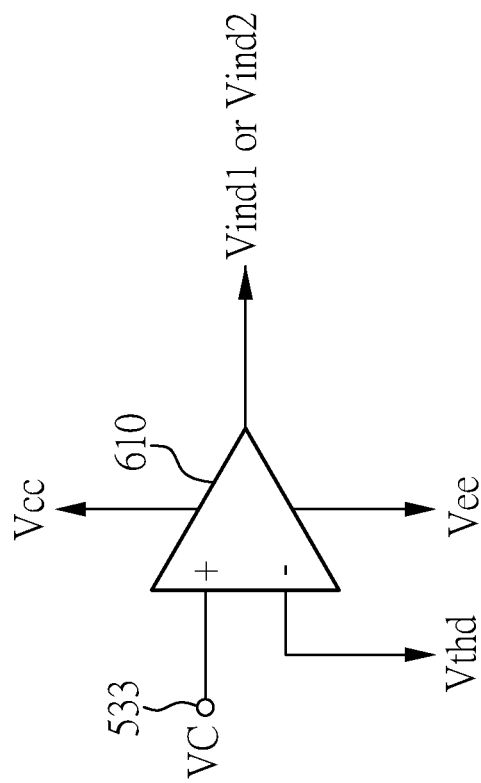
FIG. 6A is a circuit diagram of the comparator device according to the present disclosure.
Figure 6C:
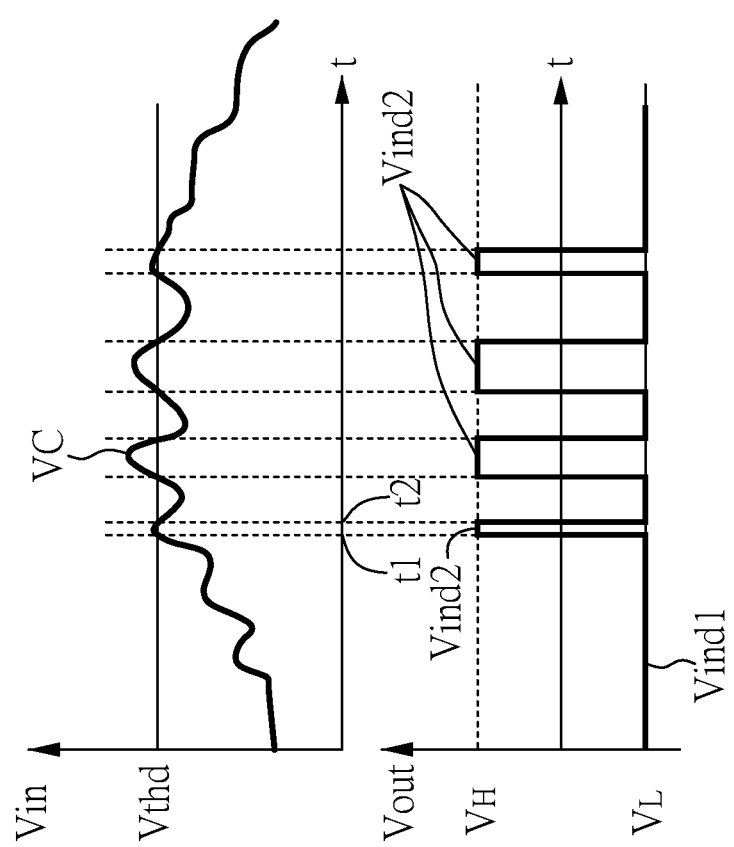
FIG. 6C is the graph showing the voltage signal and the start indication signal according to the present disclosure.

FIG. 6A is the circuit diagram of the comparator device 540 according to the present disclosure. As shown in FIG. 6A, the comparator device 540 is, for example, an operational amplifier 610, and the operational amplifier 610 has a non-inverted input terminal (+) connected to the first output terminal 533 of the switch device 530, and an inverted input terminal (−) connected to a threshold voltage Vthd. FIG. 6B is the graph showing the input/output characteristic of the operational amplifier 610 according to the present disclosure. As shown in FIG. 6B, when the voltage signal VC is larger than the threshold voltage Vthd, the operational amplifier 610 generates the second indication signal Vind2. FIG. 6C is the graph showing the voltage signal VC and the first indication signal Vind1 and second indication signal Vind2 according to the present disclosure. As shown in FIG. 6C, when the voltage signal VC is larger than the threshold voltage Vthd, the operational amplifier 610 generates the second indication signal Vind2. As shown in FIG. 6C, when the voltage signal VC is not larger than the threshold voltage Vthd, the operational amplifier 610 generates the first indication signal Vind1 (or another voltage VL). In other embodiments, the second indication signal Vind2 can be shown as a rising edge, the first indication signal Vind1 can be shown as a falling edge. In this case, in order to provide the function of the present disclosure, the relevant circuit of the controller device 560 should be modified to be edge triggered, for example, an interrupt controller of the controller device 560 should be modified from being level triggered to being edge triggered. Such modification can be achieved by one skilled in the art according to the present disclosure, and thus a detailed description therefor is deemed unnecessary.

Figure 7A:
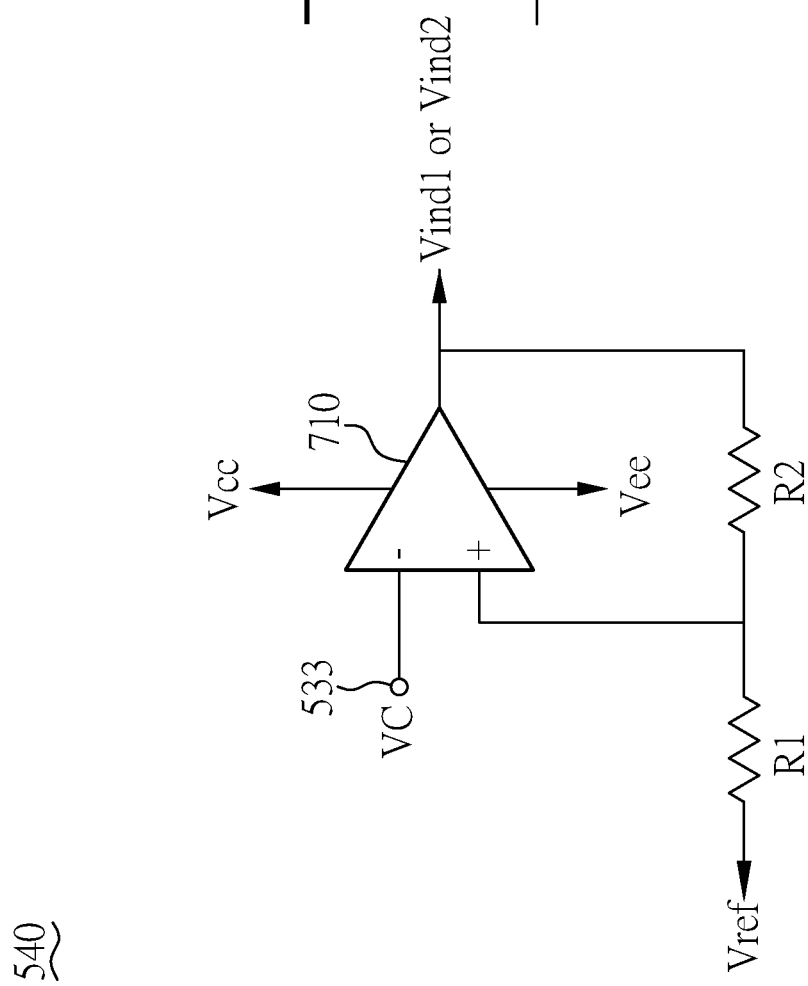
FIG. 7A is another circuit diagram of the comparator device according to the present disclosure.

FIG. 7A is another circuit diagram of the comparator device 540 according to the present disclosure. As shown in FIG. 7A, the comparator device 540 includes an operational amplifier 710, a first resistor R1 and a second resistor R2. An inverted input terminal (−) of the operational amplifier 710 is connected to the first output terminal 533 of the switch device 530. An end of the first resistor R1 is connected to a reference voltage Vref, and the other end of the first resistor R1 is connected to a non-inverted input terminal (+) of the operational amplifier 710 and an end of the second resistor R2. The other end of the second resistor R2 is connected to an output terminal of the operational amplifier 710.

Figure 7B:
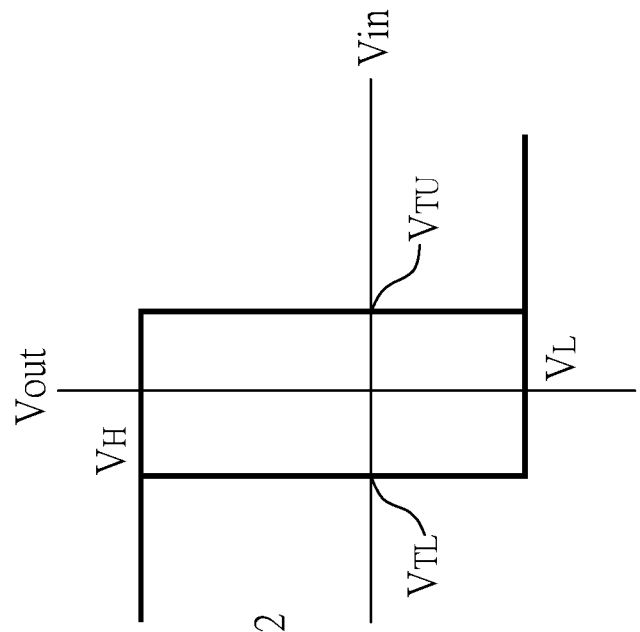
FIG. 7B is the graph showing the input/output characteristic of the comparator device according to the present disclosure.

FIG. 7B is the graph showing the input/output characteristic of the comparator device 540 of the present disclosure. As shown in 7B, there are two delay points VTU and VTL in the input/output relation of the comparator device 540. This can avoid the output of the operational amplifier 610 being frequently switched between the first indication signal Vind1 and second indication signal Vind2 in FIG. 6C. The input/output characteristic in FIG. 7B is slightly different from that in FIG. 6B. After Vin becomes larger than the delay point VTU, the output voltage is VL serving as the second indication signal Vind2. After Vin becomes smaller than the delay point VTL, the output voltage is VH serving as the first indication signal Vind1. At this time, the voltages of the first indication signal Vind1 and second indication signal Vind2 are exactly opposite to the voltages of the first indication signal Vind1 and second indication signal Vind2 in FIG. 6. However, the function of the present disclosure can be achieved by modifying the relevant circuit in the controller device 560. Such modification can be achieved by one skilled in the art according to the present disclosure, and thus a detailed description therefor is deemed unnecessary.

Figure 8:
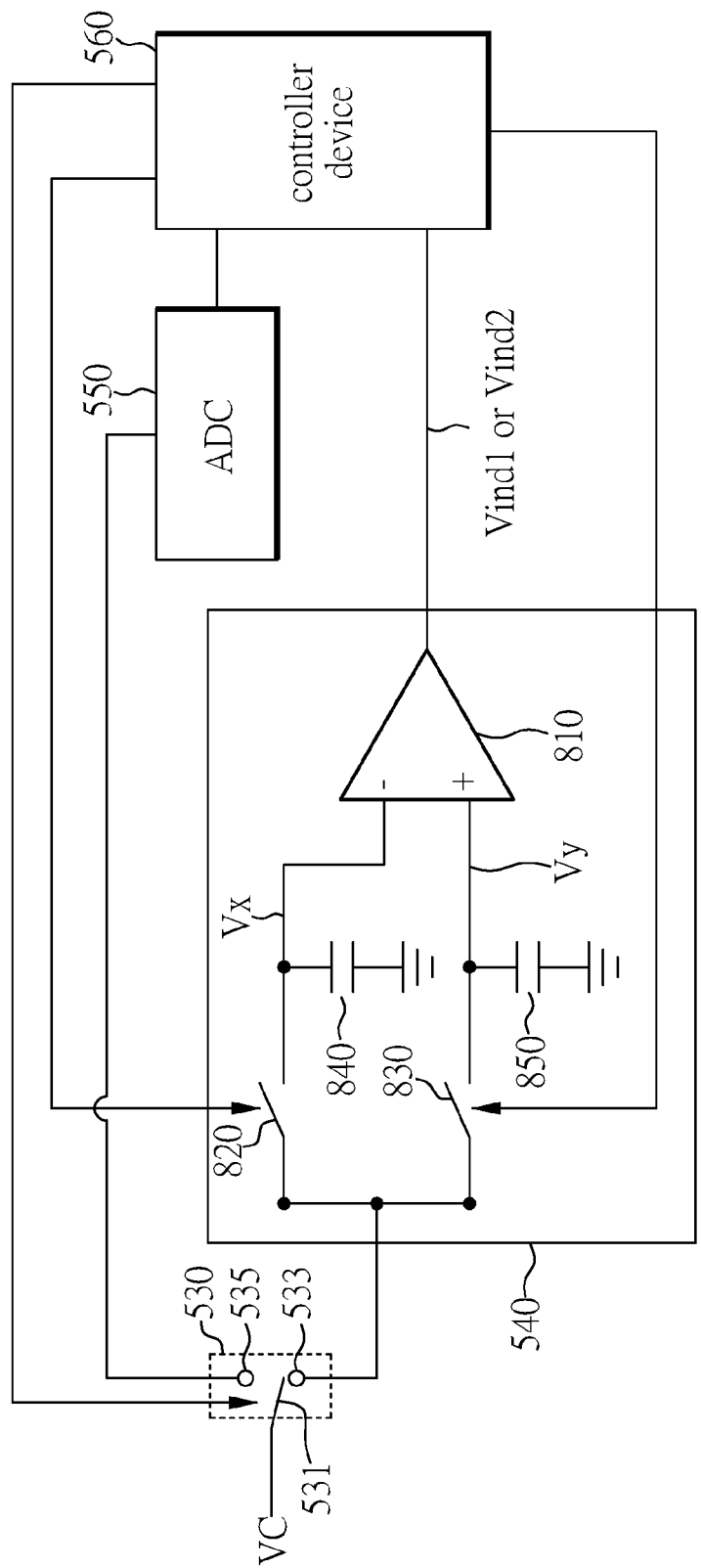
FIG. 8 is still another circuit diagram of the comparator device according to the present disclosure.

FIG. 8 is still another circuit diagram of the comparator device 540 according to the present disclosure. As shown in FIG. 8, the comparator device 540 includes an operational amplifier 810, a first sampler 820, a second sampler 830, a first capacitor 840 and a second capacitor 850. An end of the first sampler 820 is connected to the first output terminal 533 of the switch device 530, and the other end thereof is connected to an end of the first capacitor 840 and an inverted input terminal (−) of the operational amplifier 810. A control end of the first sampler 820 is connected to the controller device 560. The other end of the first capacitor 840 is connected to a low voltage (gnd). An end of the second sampler 830 is connected to the first output terminal 533 of the switch device 530, and the other end thereof is connected to an end of the second capacitor 850 and a non-inverted input terminal (+) of the operational amplifier 810. A control end of the second sampler 830 is connected to the controller device 560. The other end of the second capacitor 850 is connected to the low voltage (gnd).

The controller device 560 controls the first sampler 820 and the second sampler 830, and the sampling time of the first sampler 820 and the sample time of the second sampler 830 are non-overlapped and successive. When the X-ray radiation starts, since the sampling time of the first sampler 820 and the sample time of the second sampler 830 are non-overlapped, the sampling time of the first sampler 820 and the sample time of the second sampler 830 are different, with a certain time interval. Thus, the voltage Vx sampled by the first sampler 820 is different from the voltage Vy sampled by the second sampler 820. Accordingly, the operational amplifier 810 can generate the first indication signal Vind1 or the second indication signal Vind2.

Figure 9:
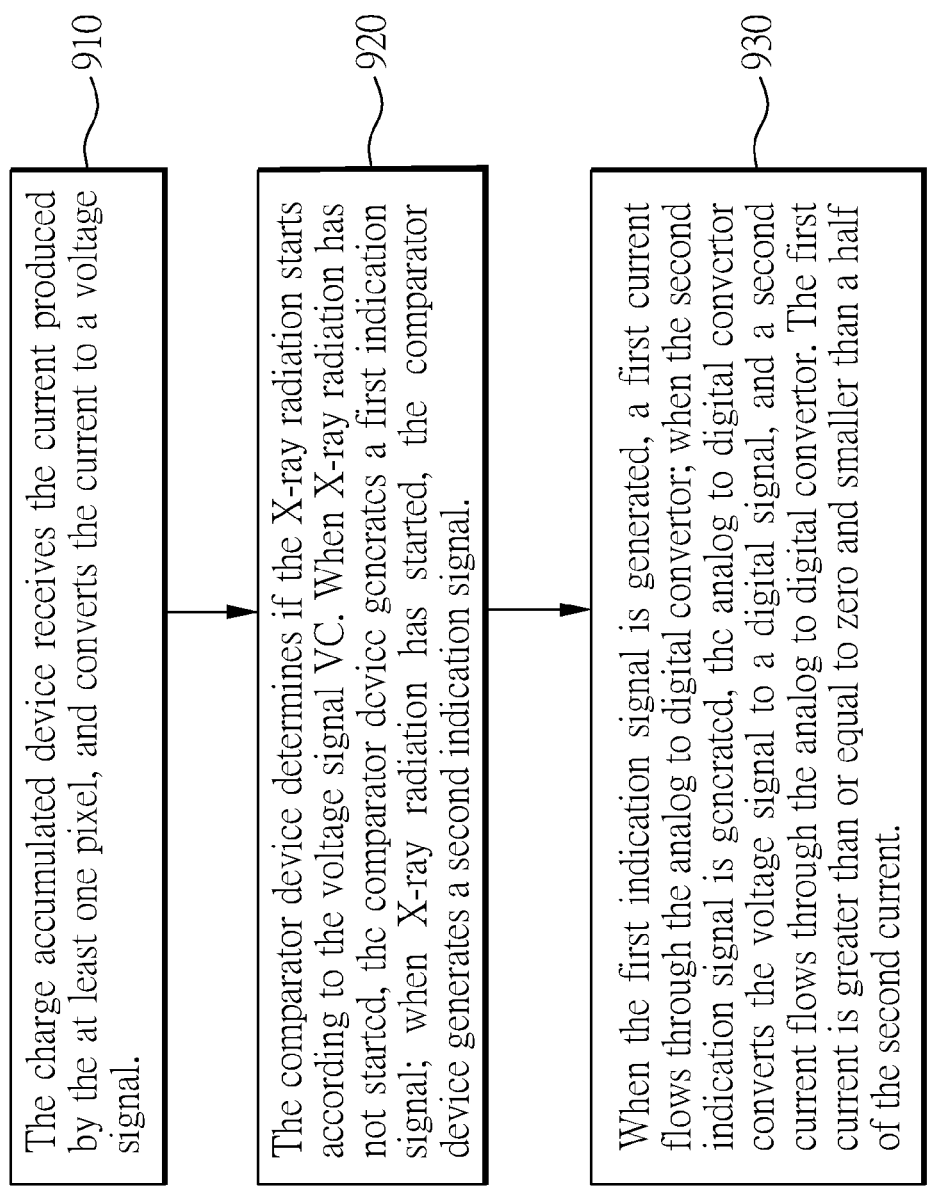
FIG. 9 is the flow chart of the method for detecting an X-ray image according to the present disclosure.

FIG. 9 is the flow chart of the method for detecting an X-ray image according to the present disclosure, which is applicable to an X-ray image detection system 500. As shown in FIG. 5, the X-ray image detection system 500 includes an X-ray image detector 510, a charge accumulation device 520, a comparator device 540 and an analog to digital convertor 550. The X-ray image detector 510 has at least one pixel 511, the at least one pixel 511 produces an amount of current corresponding to an amount of incident X-ray. In the method for detecting an X-ray image, first, in the step 910, the charge accumulation device 520 receives the current produced by the at least one pixel 511, and converts the current to a voltage signal VC. In the step 920, the comparator device 540 determines if the X-ray radiation starts according to the voltage signal VC. When X-ray radiation has not started, the comparator device 540 generates a first indication signal Vind1; when X-ray radiation has started, the comparator device 540 generates a second indication signal Vind2. In the step 930, when the first indication signal Vind1 is generated, a first current flows through the analog to digital convertor 550; when the second indication signal Vind2 is generated, the analog to digital convertor 550 converts the voltage signal to a digital signal, and a second current flows through the analog to digital convertor 550. The first current is greater than or equal to zero, and is smaller than a half of the second current.

In view of the foregoing, it is known that, during the first period in which the input terminal 531 is connected to the first output terminal 533, the comparator device 540 continuously monitors the change of the voltage signal VC, so as to determine if the X-ray radiation starts, whereas the analog to digital convertor 550 is in the sleep mode to save power. When there is no X-ray radiation, it keeps on operating in the first period (the input terminal 531 keeps connecting to the first output terminal 533). When the X-ray radiation starts, during the second period in which the input terminal 531 is connected to the second output terminal 535, the analog to digital convertor 550 is in the operating mode, so as to convert the current produced by the at least one pixel 511 to a digital signal, thereby generating X-ray image data of a patient. After receiving X-ray image data of the patient, the controller device 560 controls the input terminal 531 to connect to the first output terminal 533, and the analog to digital convertor 550 enters the sleep mode. The second period is relatively short compared to the first period, which is quite long. Thus, the present disclosure can save power efficiently.

In the application of a portable X-ray FPD, it is very important to consider about power consumption. The battery of a prior portable X-ray FPD can maintain its power for only few hours. It is inconvenient to a doctor when using it. On the contrary, the technology of the present disclosure can save power, and thus is particularly suitable for a portable X-ray FPD.

The aforementioned embodiments are examples for description, and the scope of the present disclosure is accorded to the claims as claimed hereinafter, and is not limited to the aforementioned embodiments.

What is claimed is:

1. An X-ray image detection system, comprising:
   a charge accumulation device for receiving a current produced by at least one pixel, and converting the current to a voltage signal;
   a switch device having an input terminal, a first output terminal and a second output terminal, the input terminal being connected to the charge accumulation device for receiving the voltage signal;
   a comparator device connected to the first output terminal for generating a first indication signal or a second indication signal according to the voltage signal; and
   a first analog to digital converter connected to the second output terminal,
   wherein, when the first indication signal is generated, the input terminal of the switch device is connected to the first output terminal of the switch device, when the second indication signal is generated, the input terminal of the switch device is connected to the second output terminal of the switch device.

2. The X-ray image detection system as claimed in claim 1, wherein when the input terminal of the switch device is connected to the first output terminal of the switch device, a first current flows through the first analog to digital converter; when the input terminal of the switch device is connected to the second output terminal thereof, a second current flows through the first analog to digital converter; the first current is greater than or equal to zero, and is smaller than a half of the second current.

3. The X-ray image detection system as claimed in claim 1, further comprising:
   an X-ray image detector having at least one pixel, the pixel including a switch element, an amount of current produced by the at least one pixel corresponding to an amount of incident X-ray, the switch element being connected to the charge accumulation device for transferring the current produced by the pixel to the charge accumulation device; and
   a controller device connected to the switch device, the comparator device and the first analog to digital converter.

4. The X-ray image detection system as claimed in claim 1, wherein the comparator device is a second analog to digital convertor, and a resolution of the second analog to digital convertor is lower than a resolution of the first analog to digital converter.

5. The X-ray image detection system as claimed in claim 1, wherein the comparator device is an operational amplifier having a non-inverted input terminal connected to the first output terminal of the switch device and an inverted input terminal connected to a threshold voltage, and when the voltage signal is greater than the threshold voltage, the operational amplifier generates the second indication signal.

6. The X-ray image detection system as claimed in claim 1, wherein the comparator device includes an operational amplifier, a first resistor and a second resistor, wherein an inverted input terminal of the operational amplifier is connected to the first output terminal of the switch device, an end of the first resistor is connected to a reference voltage, the other end of the first resistor is connected to a non-inverted input terminal of the operational amplifier and an end of the second resistor, and the other end of the second resistor is connected to an output terminal of the operational amplifier.

7. The X-ray image detection system as claimed in claim 6, wherein there are two delay points in an input/output relation in the comparator device.

8. The X-ray image detection system as claimed in claim 3, wherein the comparator device includes an operational amplifier, a first sampler, a second sampler, a first capacitor, and a second capacitor, wherein an end of the first sampler is connected to the first output terminal of the switch device, the other end of the first sampler is connected to an end of the first capacitor and an inverted input terminal of the operational amplifier, a control end of the first sampler is connected to the controller device, and the other end of the first capacitor is connected to a low voltage, wherein an end of the second sampler is connected to the first output terminal of the switch device, the other end of the second sampler is connected to an end of the second capacitor and a non-inverted input terminal of the operational amplifier, an control end of the second sampler is connected to the controller device, and the other end of the second capacitor is connected to the low voltage.

9. The X-ray image detection system as claimed in claim 8, wherein the controller device controls the first sampler and the second sampler, and a sampling time of the first sampler and a sampling time of the second sampler are non-overlapped.

10. A method for detecting an X-ray image, which is applicable to an X-ray image detection system including an X-ray image detector, a charge accumulation device, a comparator device and an analog to digital converter, the X-ray image detector having at least one pixel, the at least one pixel producing an amount of current corresponding to an amount of incident X-ray, the method comprising the steps of:
   using the charge accumulation device to receive the amount of current produced by the at least one pixel, and convert the amount of current to a voltage signal;
   using the comparator device to determine if the X-ray radiation starts according to the voltage signal, so as to generate a first indication signal when the X-ray radiation has not started, or to generate a second indication signal when the X-ray radiation has started;
   enabling a first current to flow through the analog to digital converter when the first indication signal is generated; enabling a second current to flow through the analog to digital converter when the second indication signal is generated, and using the analog to digital converter to convert the voltage signal to a digital signal, wherein the first current is greater than or equal to zero, and is smaller than a half of the second current.

11. The method for detecting an X-ray image as claimed in claim 10, the X-ray image detection system further comprising a switch device having an input terminal, a first output terminal and a second output terminal, the input terminal being connected to the charge accumulation device for receiving the voltage signal;

wherein, when the first indication signal is generated, the input terminal of the switch device is connected to the first output terminal of the switch device, and when the second indication signal is generated, the input terminal of the switch device is connected to the second output terminal of the switch device.

12. The method for detecting an X-ray image as claimed in claim 11, the X-ray image detection system further comprising a controller device connected to the switch device, the comparator device and the first analog to digital converter, wherein when the controller device receives the first indication signal, it controls the input terminal of the switch device to connect to the first output terminal, and when the controller device receives the second indication signal, it controls the input terminal of the switch device to connect to the second output terminal.

* * * * *